United States Patent
Trimmer et al.

(10) Patent No.: US 9,861,487 B2
(45) Date of Patent: Jan. 9, 2018

(54) TOTAL KNEE FEMORAL COMPONENT WITH FLEXIBLE ANTERIOR FLANGE

(71) Applicant: Howmedica Osteonics Corp., Mahwah, NJ (US)

(72) Inventors: Kenneth Trimmer, Waldwick, NJ (US); Vincent Alipit, Nanuet, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 22 days.

(21) Appl. No.: 15/010,957

(22) Filed: Jan. 29, 2016

(65) Prior Publication Data

US 2017/0216040 A1    Aug. 3, 2017

(51) Int. Cl.
*A61F 2/38* (2006.01)
*A61F 2/40* (2006.01)

(52) U.S. Cl.
CPC ............ *A61F 2/3859* (2013.01); *A61F 2/389* (2013.01); *A61F 2/4014* (2013.01); *A61F 2/4081* (2013.01); *A61F 2310/00011* (2013.01)

(58) Field of Classification Search
CPC ......................... A61F 2/3859; A61F 2002/3474
See application file for complete search history.

(56) References Cited

U.S. PATENT DOCUMENTS

| | | | |
|---|---|---|---|
| 4,215,439 A | 8/1980 | Gold et al. | |
| 5,507,820 A | 4/1996 | Pappas | |
| 5,702,460 A * | 12/1997 | Carls | A61B 17/155 606/79 |
| 6,827,739 B2 | 12/2004 | Griner et al. | |
| 7,105,026 B2 | 9/2006 | Johnson et al. | |
| 7,150,761 B2 | 12/2006 | Justin et al. | |
| 7,258,701 B2 | 8/2007 | Aram et al. | |
| 7,297,164 B2 | 11/2007 | Johnson et al. | |
| 7,520,901 B2 | 4/2009 | Engh et al. | |
| 7,527,650 B2 | 5/2009 | Johnson et al. | |
| 7,615,081 B2 | 11/2009 | Justin et al. | |
| 7,799,084 B2 | 9/2010 | Clemow et al. | |
| 7,896,922 B2 | 3/2011 | Engh et al. | |

(Continued)

*Primary Examiner* — Thomas J Sweet
*Assistant Examiner* — Megan Wolf
(74) *Attorney, Agent, or Firm* — Lerner, David, Littenberg, Krumholz & Mentlik, LLP

(57) ABSTRACT

Prostheses that address stress shielding are disclosed. For instance, a knee prosthesis includes a monolithic femoral component having medial and lateral condylar elements for confronting and engaging a natural tibia or a bearing member of a tibial component, an intercondylar notch between the condylar elements for confronting and engaging a natural patella or a patellar component, and an anterior flange extending proximally from the medial and lateral condylar elements and the intercondylar notch. The femoral component defines a bone-facing surface and a bearing surface, the bearing surface including medial and lateral condylar articular surfaces defined by the medial and lateral condylar elements, respectively, and an intercondylar articular surface defined by the intercondylar notch. A slot extends through the femoral component from the bearing surface to the bone-facing surface, the slot starting at an edge of the femoral component and ending at a location within the anterior flange. Methods of making and using the prosthesis are also provided.

17 Claims, 9 Drawing Sheets

(56) References Cited

U.S. PATENT DOCUMENTS

| | | |
|---|---|---|
| 8,002,840 B2 | 8/2011 | Aram et al. |
| 8,048,163 B2 | 11/2011 | Coon et al. |
| 8,236,060 B2 | 8/2012 | Justin et al. |
| 8,460,391 B2 | 6/2013 | Justin et al. |
| 8,475,535 B2 | 7/2013 | Otto |
| 8,535,383 B2 | 9/2013 | Aram et al. |
| 8,603,091 B2 | 12/2013 | Lutz et al. |
| 8,808,386 B2 | 8/2014 | Engh et al. |
| 9,072,605 B2 | 7/2015 | Coon et al. |
| 2005/0278034 A1 | 12/2005 | Johnson et al. |
| 2006/0009853 A1 | 1/2006 | Justin et al. |
| 2006/0167462 A1* | 7/2006 | Raugel ............... A61F 2/34 606/91 |
| 2007/0043444 A1 | 2/2007 | Lester |
| 2007/0173858 A1 | 7/2007 | Engh et al. |
| 2011/0144760 A1 | 6/2011 | Wong et al. |
| 2011/0218541 A1* | 9/2011 | Bailey ............... A61B 17/56 606/88 |
| 2011/0307067 A1* | 12/2011 | Dees ............... A61B 17/155 623/20.35 |
| 2016/0030198 A1* | 2/2016 | Enomoto ........... A61F 2/4684 623/20.35 |
| 2017/0020689 A1* | 1/2017 | Asmus ............... A61F 2/3836 |

\* cited by examiner

TOTAL KNEE FEMORAL COMPONENT WITH FLEXIBLE ANTERIOR FLANGE

BACKGROUND OF THE INVENTION

The present invention relates to flexible prosthetic devices and methods of making such devices. More particularly, the present invention relates to a knee prosthesis having a femoral component in which a slot allows for added flexibility between different aspects or portions of the component, as well as the methods associated with making and using the prosthesis.

A current concern with modern total knee arthroplasty is femoral bone resorption due to stress shielding. This is most commonly found in the distal/anterior region of the femoral bone behind the patellar groove of an implant. Solid femoral components, most commonly manufactured from cobalt chromium alloy, have a significantly higher modulus of elasticity than the underlying bone. Additionally, most femoral components are rigid due to the amount of solid material that encompasses the space between the articular surface and the surfaces that mate with the resected femur.

Wolff's law states that bone remodels in the presence of load. In the natural knee, the articular surfaces are loaded by the patella and tibia. Replacing that bearing with a stiff metal component shields the underlying bone from much of the load in the anterior and posterior regions, leading to a lack of remodeling and ultimately, resorption. This bone resorption due to stress shielding may also occur in connection with other arthroplasty procedures.

Currently, the only products that have been offered to address this issue are solid femoral components fabricated from titanium with the same geometry as the existing cobalt chromium versions. Although titanium has a lower modulus of elasticity than cobalt chrome, it is still significantly higher than bone, providing only a limited reduction in stress shielding. Additionally, titanium has been proven to be a poor bearing material and subsequent treatments of the bearing surface would be necessary to provide sufficient wear characteristics. These subsequent treatments can add significant cost and complexity to the manufacturing process.

Thus, there exists a need for a more effective solution to the problem of stress shielding, particularly in the distal/anterior femoral bone, that improves upon these shortcomings.

BRIEF SUMMARY OF THE INVENTION

A first aspect of the present invention is a prosthesis including a body including an articular surface and a bone-contacting surface opposite the articular surface. The articular and bone-contacting surfaces are located within an edge of the body. A slot extends through the articular and bone contacting surfaces. A first end of the slot passes through the edge and a second end of the slot is located away from the edge.

In accordance with other embodiments of the first aspect, the body may be a femoral component, and the articular surface may include medial and lateral condylar articular surfaces and an intercondylar articular surface. The slot may partially disconnect the medial and lateral condylar articular surfaces to define a cantilever beam including the intercondylar articular surface. The body may be flexibly configured to transfer loads from the articular surface directly to the resected femoral bone. The slot may at least partially separate the medial condylar articular surfaces from the cantilever beam.

The body may be comprised of a metallic material. The body may be a humeral or glenoid component. A width of the slot may be less than 10% of a width of the entire body measured along the same direction. A width of the slot may be substantially constant along a majority of a length of the slot. A dimension of the slot at the second end may be larger than the substantially constant width of the slot.

A second aspect of the present invention is a knee prosthesis including a monolithic femoral component including medial and lateral condylar elements for confronting and engaging a natural tibia or a bearing member of a tibial component, an intercondylar notch between the medial and lateral condylar elements for confronting and engaging a natural patella or a patellar component, and an anterior flange extending proximally from the medial and lateral condylar elements and the intercondylar notch. The femoral component defines a bone-facing surface and a bearing surface, the bearing surface including medial and lateral condylar articular surfaces defined by the medial and lateral condylar elements, respectively, and an intercondylar articular surface defined by the intercondylar notch. A slot extends through the femoral component from the bearing surface to the bone-facing surface, the slot starting at an edge of the femoral component and ending at a location within the anterior flange.

In accordance with other embodiments of the second aspect, the slot may start at a medial-distal intersection of the intercondylar notch and the medial condyle and may extend proximally along a medial edge of the intercondylar notch. The slot may further extend laterally along a proximal region of the anterior flange. The slot may partially disconnect the medial and lateral condylar articular surfaces to define the intercondylar notch as a cantilever beam. The femoral component may be flexibly configured to transfer loads from the bearing surface directly to the resected femoral bone, particularly that beneath the anterior flange. The slot may at least partially separate the medial condylar element from the cantilever beam.

The femoral component may be comprised of a metallic material. The knee prosthesis may further include a tibial component including a bearing member. The knee prosthesis may further include a patellar component. A width of the slot may be less than 10% of a width of the femoral component measured along the same direction. A width of the slot may be substantially constant along a majority of a length of the slot. A dimension of the slot at the location within the anterior flange at which the slot ends may be larger than the substantially constant width of the slot. The slot may extend along a path that is generally "L" shaped. The slot may extend along a path from a location at the edge of the femoral component to the end location within the anterior flange that measures at least ten times a width of the slot.

A third aspect of the present invention is a method of making a knee prosthesis, including the steps of cutting a slot in a monolithic femoral component, which includes medial and lateral condylar elements for confronting and engaging a natural tibia or a bearing member of a tibial component, an intercondylar notch between the medial and lateral condylar elements for confronting and engaging a natural patella or a patellar component, and an anterior flange extending proximally from the medial and lateral condylar elements and the intercondylar notch, wherein the femoral component defines a bone-facing surface and a bearing surface, the bearing surface including medial and lateral condylar articular surfaces defined by the medial and lateral condylar elements, respectively, and an intercondylar articular surface defined by the intercondylar notch. The step of cutting includes cutting the slot to extend through the femoral component from the bearing surface to the bone-facing surface, and cutting the slot such that the slot starts at an edge of the femoral component and ends at a location within the anterior flange.

In accordance with other embodiments of the third aspect, the step of cutting may further include cutting the slot such that the slot starts at a medial-distal intersection of the intercondylar notch and the medial condyle and extends proximally along a medial edge of the intercondylar notch. The step of cutting may further include cutting the slot such that the slot extends laterally along a proximal region of the anterior flange. The step of cutting may include cutting the material of the femoral component with a laser, wire, drill, burr, saw, or endmill.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
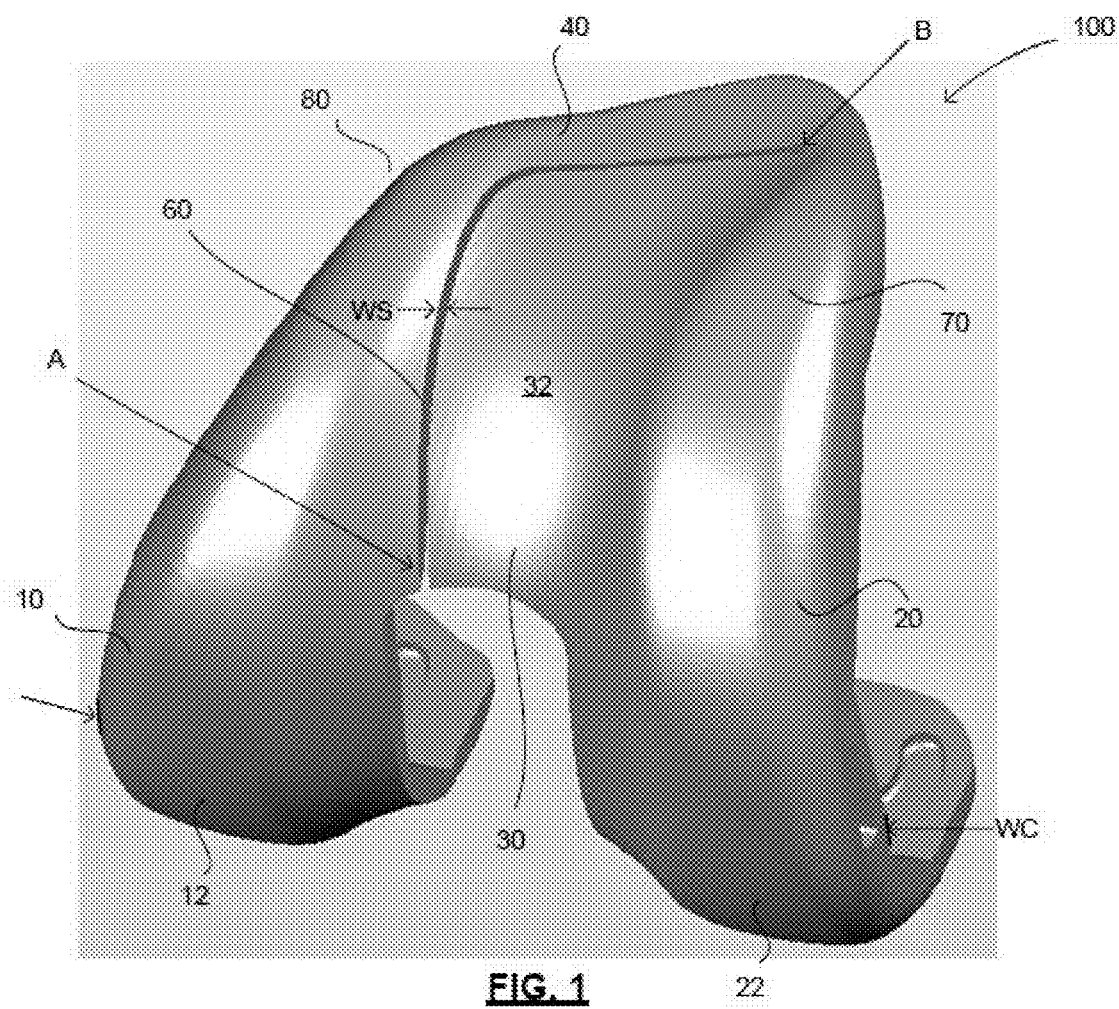
FIG. 1 is a distal perspective view of a femoral component of a knee prosthesis in accordance with one embodiment of the present invention.
Figure 2:
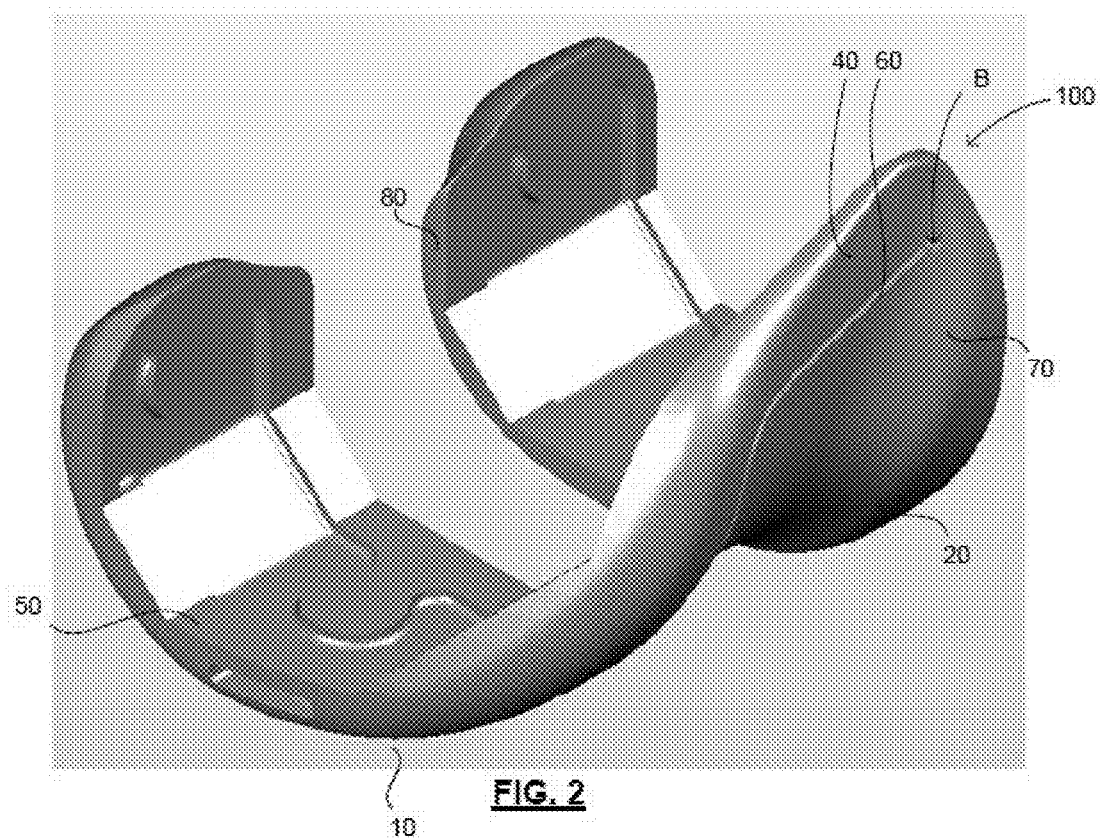
FIG. 2 is a proximal perspective view of the femoral component shown in FIG. 1.

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents that operate in a similar manner to accomplish similar purpose.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Referring to FIGS. 1-6, there is shown a femoral component 100 of a knee prosthesis in accordance with one embodiment of the present invention. Femoral component 100 is a body that replaces the articular surface of the distal femur and includes a medial condylar element 10, a lateral condylar element 20, an intercondylar notch 30, and an anterior flange 40 extending proximally from the medial and lateral condylar elements 10, 20 and intercondylar notch 30. Medial and lateral condylar elements 10, 20 confront and engage either a bearing member of a tibial component or a natural tibia, if femoral component 100 component is used without a tibial component. Intercondylar notch 30 is disposed between medial and lateral condylar elements 10, 20 and confronts and engages a patellar component or a natural patella, if femoral component 100 component is used without a patellar component.

Femoral component 100 defines a bone-facing or bone-contacting surface 50 that fixes the implant to the prepared distal femur. Opposite bone-facing surface 50 is a bearing or articular surface 70, which includes medial and lateral condylar articular surfaces 12, 22 defined by medial and lateral condylar elements 10, 20, respectively, and an intercondylar articular surface 32 defined by intercondylar notch 30.

A slot 60 extends through femoral component 100 from articular surface 70 to bone-facing surface 50. That is, slot 60 cuts through the thickness of femoral component 100 defined between articular surface 70 to bone-facing surface 50 such that it extends through both of those surfaces. Slot 60 starts at a first location A at an edge 80 of femoral component 100 and ends at a location B within anterior flange 40. Location A where slot 60 starts or cuts or passes through edge 80 is at a medial-distal intersection of intercondylar notch 30 and medial condylar element 10. Slot 60 extends from location A proximally along a medial edge of intercondylar notch 30, or the patellar track. Slot 60 then extends laterally along a proximal region of anterior flange 40 until it ends at location B, which is away from edge 80 and does not cut or pass through edge 80. Of course, this is but one orientation and configuration for slot 60 and other embodiments may include a slot positioned in different locations, exhibiting a different shape or both. While it is noted that slot 60 extends through articular surface 70, the location of slot 60 is selected so that it does not interfere with the areas of articular surface 70 that typically come into contact with mating surfaces.

In the particular embodiment shown, slot 60 partially disconnects the medial and lateral condylar articular surfaces 12, 22 to define intercondylar notch 30 as a cantilever beam. In other words, slot 60 at least partially separates medial condylar element 10 from the cantilever beam. In this way, the medial side of the patella track is disconnected to allow cantilever bending of the patella track under load. This allows femoral component 100 to be flexibly configured to transfer loads from articular surface 70 directly to the resected femoral bone, particularly that portion of the resected femoral bone that is beneath anterior flange 40, by providing it with a flexible patella-femoral articular surface.

Bone-facing surface 50 and the opposed articular surface 70 are both located and confined within edge 80 of the body, which is a perimeter or boundary of the body that defines its footprint on the resected bone. The material of the body takes up a defined volume of space that is bounded by bone-facing surface 50, articular surface 70, and edge 80. Edge 80 follows the contour at the perimeter of the material that makes up the body of femoral component 100. In this regard, edge 80 ignores slot 60 such that the path of edge 80 traverses the starting location of slot 60 at location A. In other words, edge 80 follows a path of femoral component 100 as if slot 60 was not present.

In a preferred embodiment, a width WS of slot 60 is less than 10% of a width WC of femoral component 100 when measured along the same direction. In another preferred embodiment, width WS is less than 5% of width WC. In yet another preferred embodiments, width WS is less than 2% of width WC. In these and/or other embodiments, slot width WS is sufficiently wide to partially separate medial and lateral condylar elements 10, 20, but sufficiently narrow as to infringe on the contact area of the mating natural patella or patella implant or natural tibia or tibial insert. Width WS of slot 60 is substantially constant along a majority (such as at least 90%) of a length of slot 60. That is, the distance separating interior side walls of slot 60 remains substantially constant along the path or length of slot 60. That distance or width WS of a portion of slot 60 is measured perpendicularly to an axis along which the path of slot 60 extends or to which the path of slot 60 is tangent at that measured portion of slot 60. Thus, while the path of slot 60 may not be axial and may curve, the width of slot 60 remains substantially constant. In other embodiments, the width of slot 60 may vary at some or all locations along its path.

Figure 3:
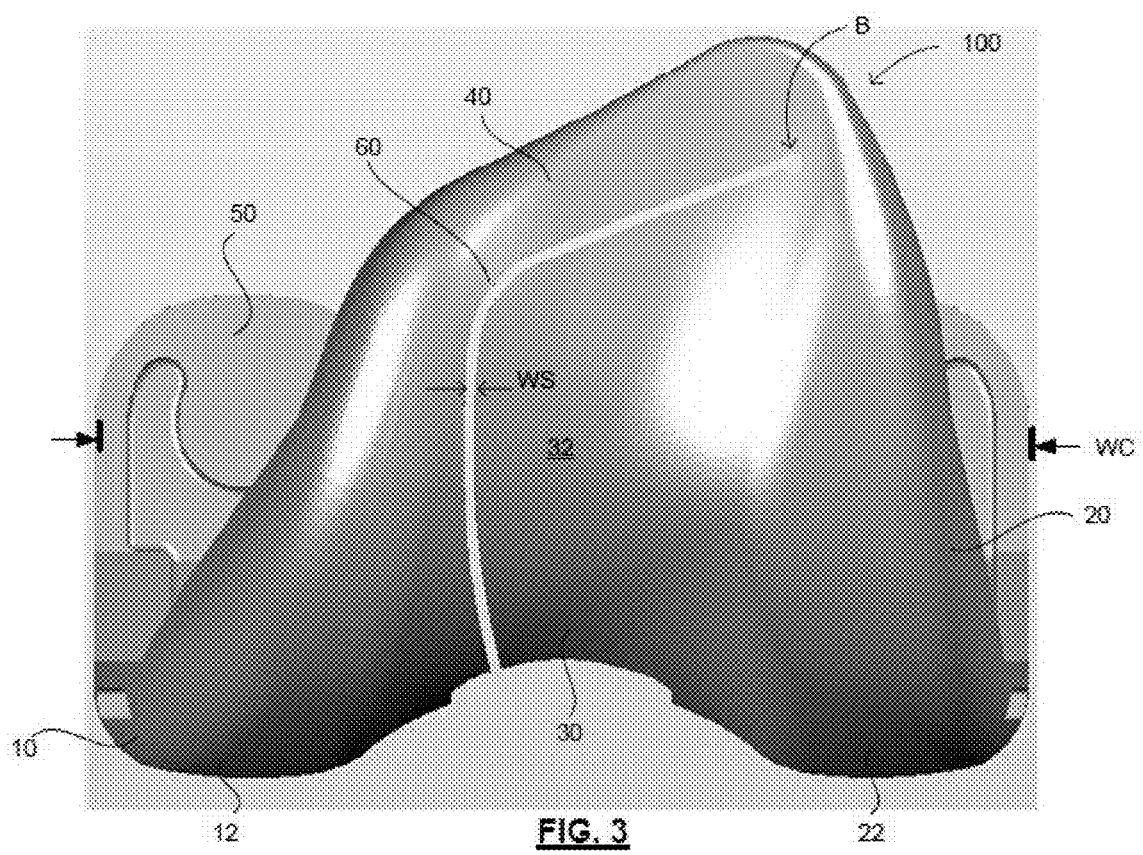
FIG. 3 is an anterior plan view of the femoral component shown in FIG. 1.
Figure 4:
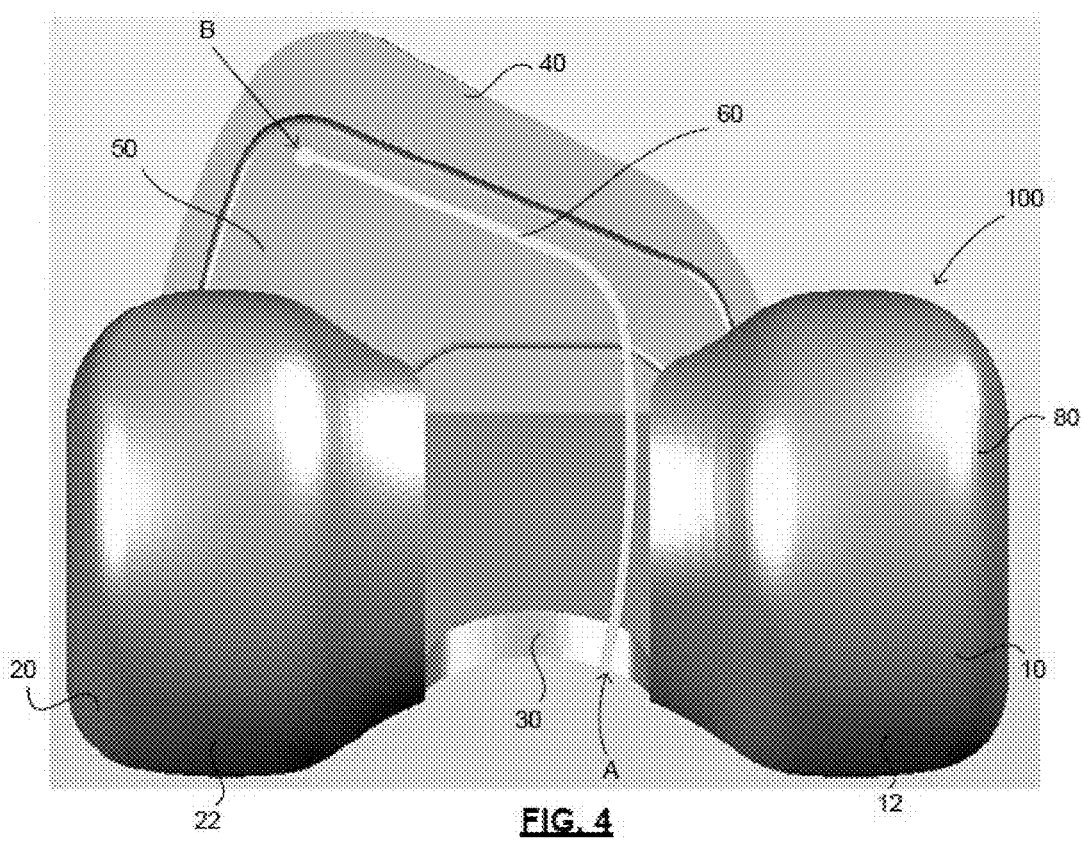
FIG. 4 is a posterior plan view of the femoral component shown in FIG. 1.
Figure 5:
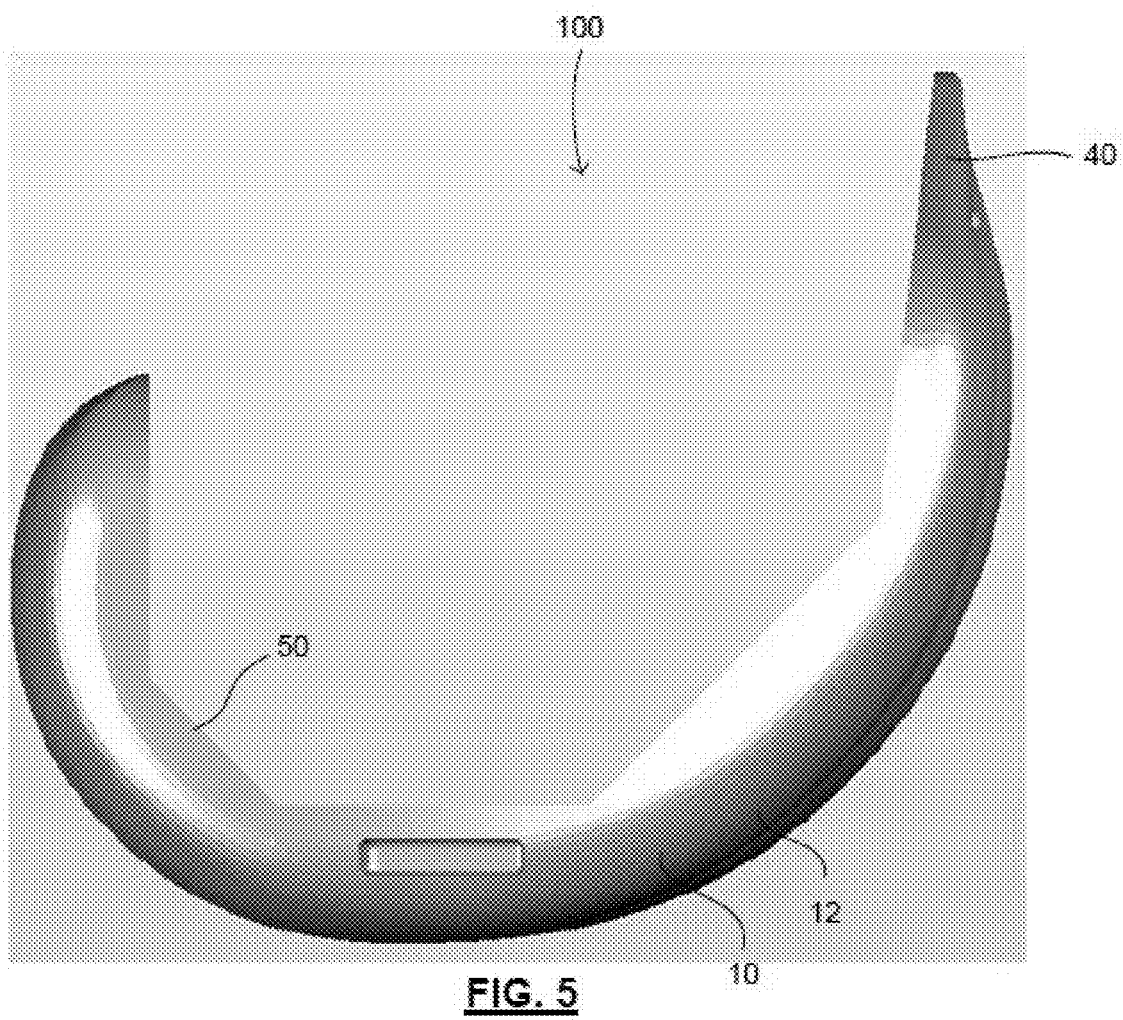
FIG. 5 is a medial plan view of the femoral component shown in FIG. 1.
Figure 6:
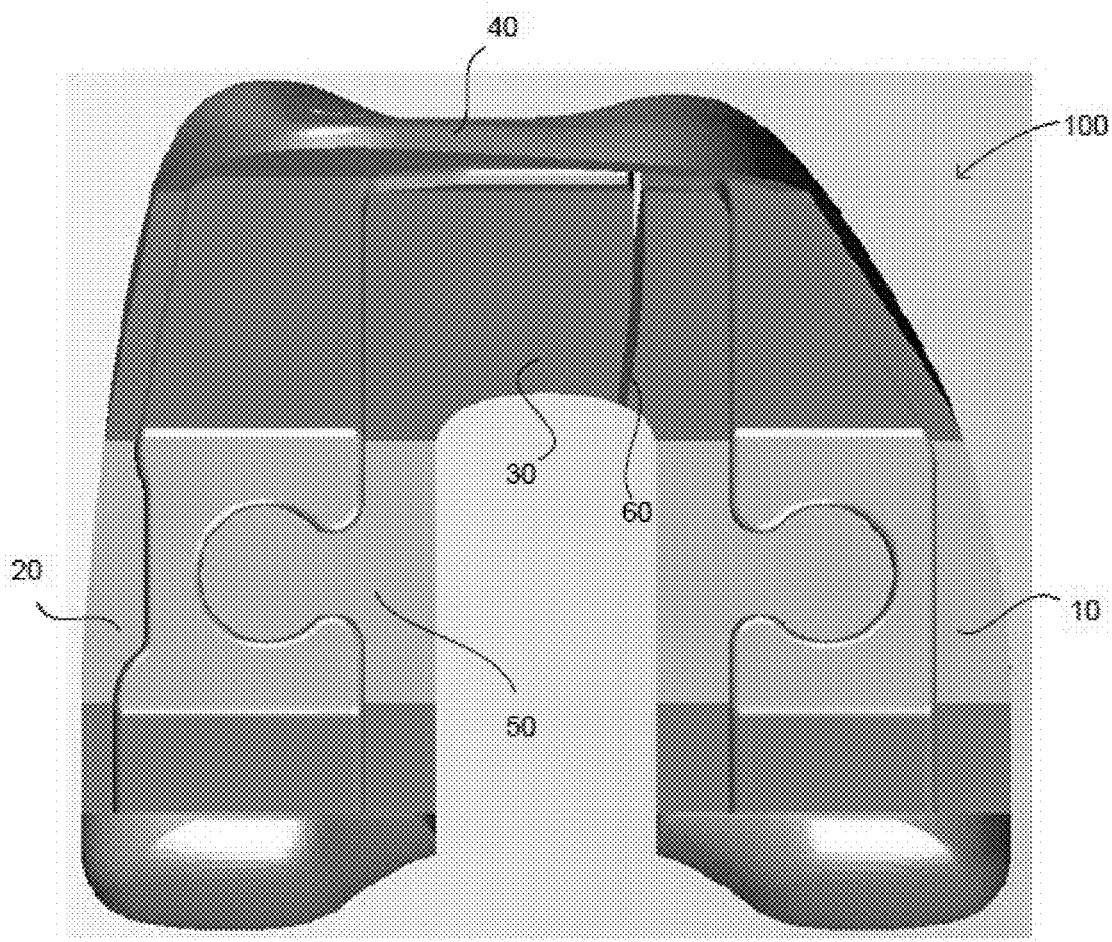
FIG. 6 is a proximal plan view of the femoral component shown in FIG. 1.

As best seen in FIGS. 3 and 4, a dimension of slot 60 at location B is larger than width WS of slot 60. That is, the dimension of slot 60 at location B can be a maximum diameter of a circular perimeter of slot 60 at location B defined in bone-facing surface 50 and articular surface 70. Such circular perimeter enlarges the dimension of the closed end of slot 60 to minimize cracking in the material of femoral component 100 adjacent location B of slot 60 due to repeated flexing of the portions of femoral component 100 adjacent slot 60.

As shown in FIGS. 1, 3, and 4, slot 60 extends along a path that is generally "L" shaped. In a preferred embodiment, slot 60 can extend along a path from location A to location B that measures at least ten times its width WS. In another preferred embodiment, slot 60 can extend along a path from location A to location B that measures at least fifty times its width WS. In another preferred embodiment, slot 60 can extend along a path from location A to location B that measures approximately seventy-six times its width WS. In yet another preferred embodiment, slot 60 can extend along a path from location A to location B that measures at least one hundred times its width WS.

The present design is based on successful contemporary total knees. The articular geometry and bone opposing geometry of femoral component 100 can be similar or identical to an existing contemporary cobalt chromium femoral component, which includes a solid articular surface. However, by adding slot 60 through the anterior flange of the femoral component, the patella track becomes, in essence, a cantilever beam. The inclusion of slot 60 allows femoral component 100 to perform in a way that solid prior art devices could not. Namely, it allows for a flexible patella-femoral articular surface, whereas prior art devices were confined to a solid articular surface. Being unsupported on one end, the patella track is no longer rigid but is now flexible, which gives it the ability to transfer the loads from the articular surfaces directly to the resected bone. Thus, a more clinically- and cost-effective solution to the problem of distal/anterior femoral stress shielding is achieved.

Femoral component 100 is made of a biocompatible material, preferably a metallic material such as cobalt chromium or titanium. Other types of biocompatible metallic materials can be used. Alternatively, femoral component 100 can be comprised of a polymeric or ceramic material. A blend of any of these biocompatible materials is also contemplated.

Femoral component 100 is monolithic, i.e. constructed from a single piece of material. This provides advantages over components in which two or more pieces are assembled together, e.g. by dovetail joints, glue, welding, or the like or by mechanical hinges or other flexible connections between two distinct and separate pieces. Construction of femoral component 100 as monolithic allows for the natural stresses and strains of the material of which flexible component 100 is comprised to dictate its flexibility when under load. The type and thickness of the material can be selected as appropriate to allow for the aspects of flexible component 100 opposite slot 60 to interact with one another as desired. This dictates and limits the amount and extent of flexible movement between the adjacent aspects based on the properties of the material of femoral component 100. This is superior to a hinged femoral component or one assembled between multiple pieces. Such a hinged or assembled component would most likely include a medial condylar element separate and distinct from a lateral condylar element, which are hinged or assembled to create a component that is otherwise similar in nature to femoral component 100. However, a mechanical hinge does not allow such a component to function as femoral component 100 can, because the flexibility of such a component is usually much greater since the hinged aspects allow for greater movement along the hinged axis. In a similar way, an assembled component of two or more pieces suffers from less stability at the point of assembly than femoral component 100, which allows stresses and strains in its material to transmit within and throughout the monolithic body of material. Thus, while certain previous components have been comprised of separate and distinct pieces in a hinged or assembled fashion, those types of components do not and cannot manipulate flexibility of the component in the way femoral component 100 can due to its monolithic construction.

The knee prosthesis that includes femoral component 100 can also include a tibial component having a bearing member and/or a patellar component. A kit of components can be provided that includes different sizes and/or shapes of femoral component 100 along with different sizes and or shapes of tibial and/or patellar components. Such a kit provides a surgeon with the ability to select an appropriately sized and shaped knee prosthesis for a particular patient.

A prosthesis can be constructed according to the present teachings to allow for a slot within any prosthetic articular component in a joint of the human or animal body to allow load to be transmitted to the resected bone beneath the implanted component. In other embodiments, the body of the prosthesis described above as femoral component 100 can a humeral or glenoid component, an acetabular component, or a tibial or talar component. A prosthesis according to the present teachings can also be based on other components of joints or other load bearing bones.

A method of using femoral component 100 includes implanting femoral component 100 to confronting and engaging a natural tibia or a bearing member of a tibial component and a natural patella or a patellar component. Once implanted, femoral component 100 performs under load to transfer such loads to the underlying bone surfaces. As the knee flexes, the greatest load in the patella femoral joint occurs between 30 and 90 degrees. Under these loads, the femoral component would flex in the region under the patella, thereby transferring load to the bone behind the anterior and anterior chamfer bone cuts. The associated stresses would maintain loading of the subchondral bone in the region behind the trochlear groove and reduce the potential for stress shielding and bone resorption.

A method of making femoral component 100 includes providing a femoral component with a solid articular surface that is otherwise configured like femoral component 100. The method includes cutting slot 60 in femoral component 100 in the path described above. Slot 60 can be cut with a laser, wire, drill, burr, saw, endmill, or any other similar device. Femoral component 100 can be finished by sanding, blasting, or otherwise removing any sharp edges and can be coated, if desired. Of course, this same type manufacturing method may also be utilized to form implants for other anatomical uses.

Additionally, it is contemplated to create an implant according to the present invention through an additive manufacturing process. This may allow for the inclusion of porous bone engaging surfaces as well, which aid in allowing bone growth between the implant and the bone on which it is implant. For instance, it is contemplated to form both any portion and solid portions of an implant such as femoral component 100 through the use of a 3D printing process such as is disclosed in U.S. Pat. Nos. 7,537,664 and 8,147,861; U.S. Patent Application Publications Nos. 2006/0147332, 2007/0142914, 2008/0004709; and U.S. patent application Ser. Nos. 13/441,154 and 13/618,218, the disclosures of which are hereby incorporated by reference herein. Of course, a slot like slot 60 could be provided in the 3D printed design, without the need for a secondary process. It is also contemplated to form any porous portion via another known or hereafter developed procedure, such as laser etching.

Figure 7:
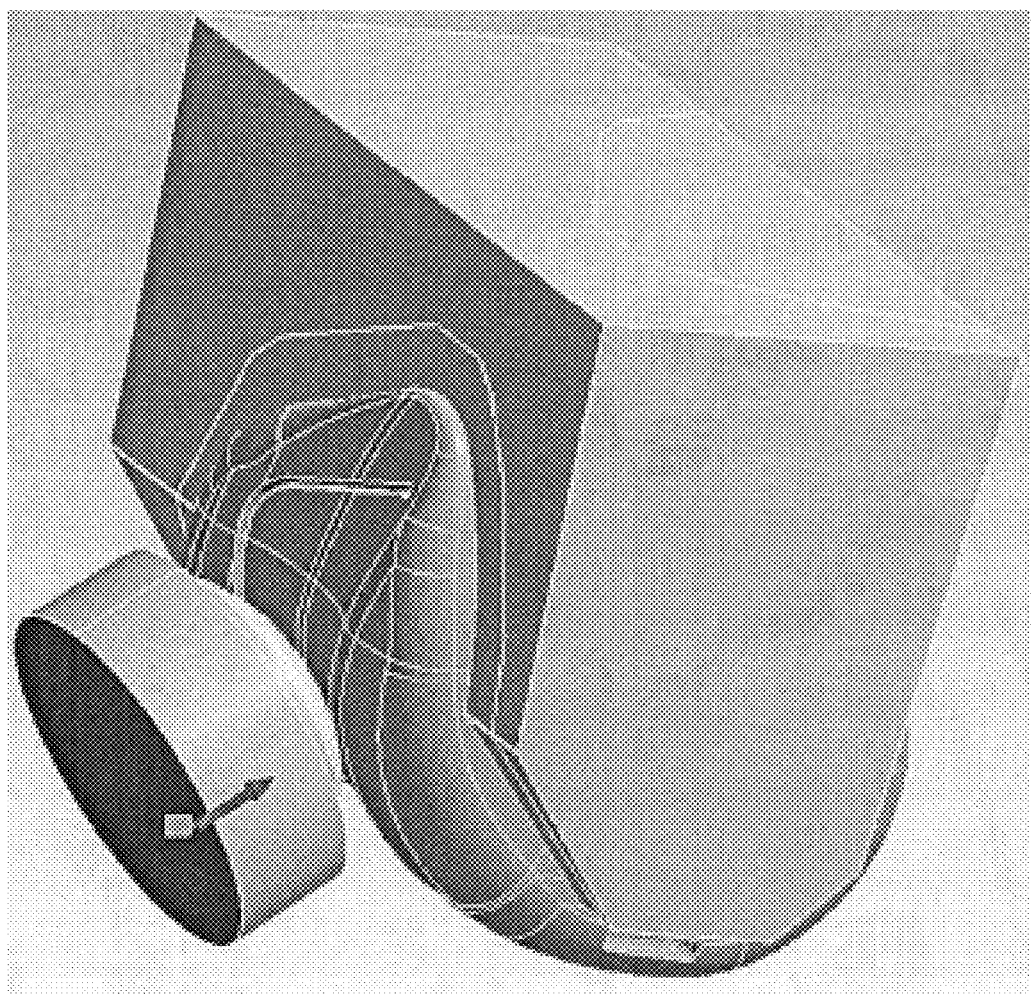
FIG. 7 is a depiction of the testing conditions of femoral components for a finite element analysis.
Figure 8:
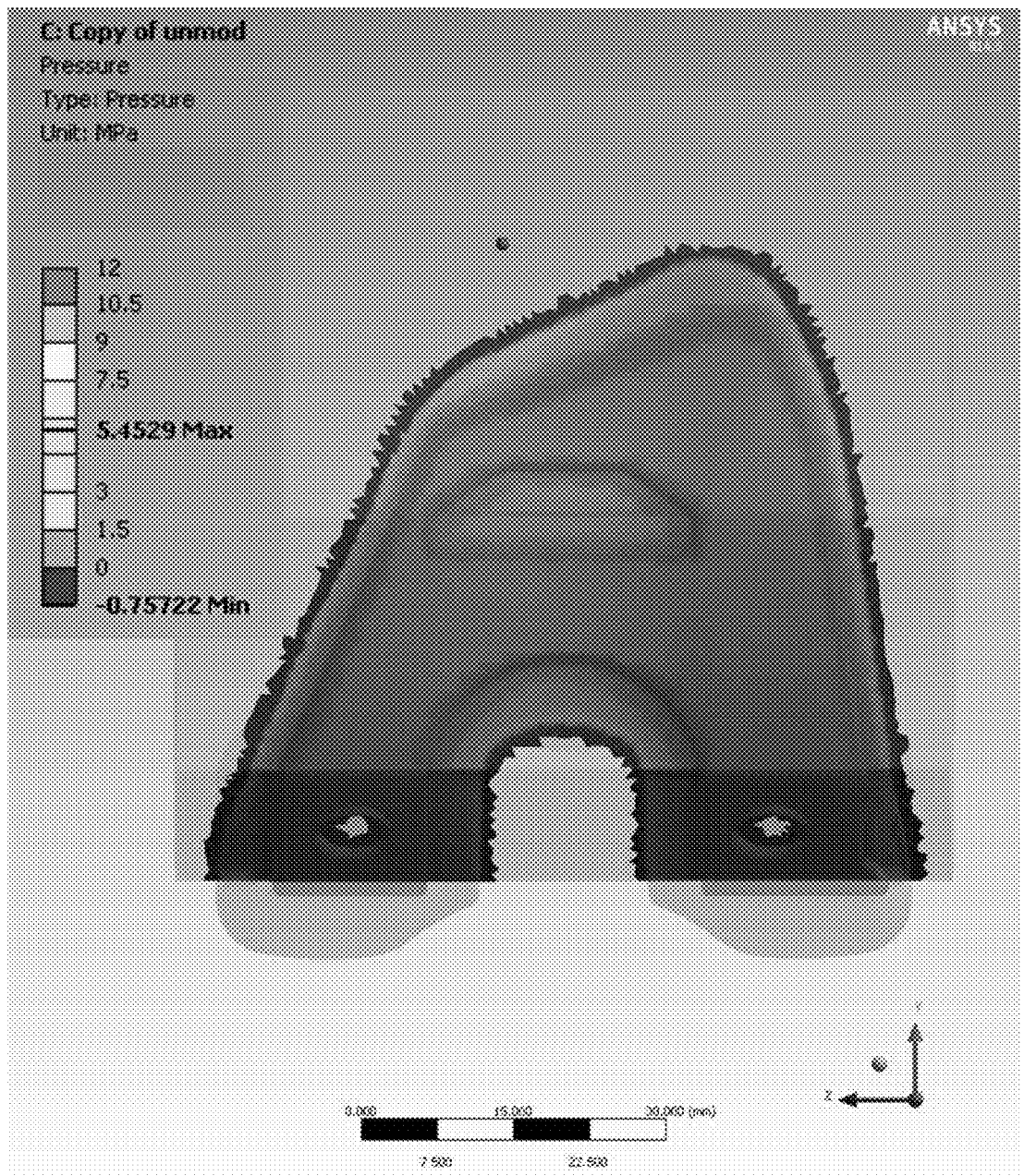
FIG. 8 is an image showing the normalized contact pressure distribution of the underlying bone upon testing a standard femoral component.
Figure 9:
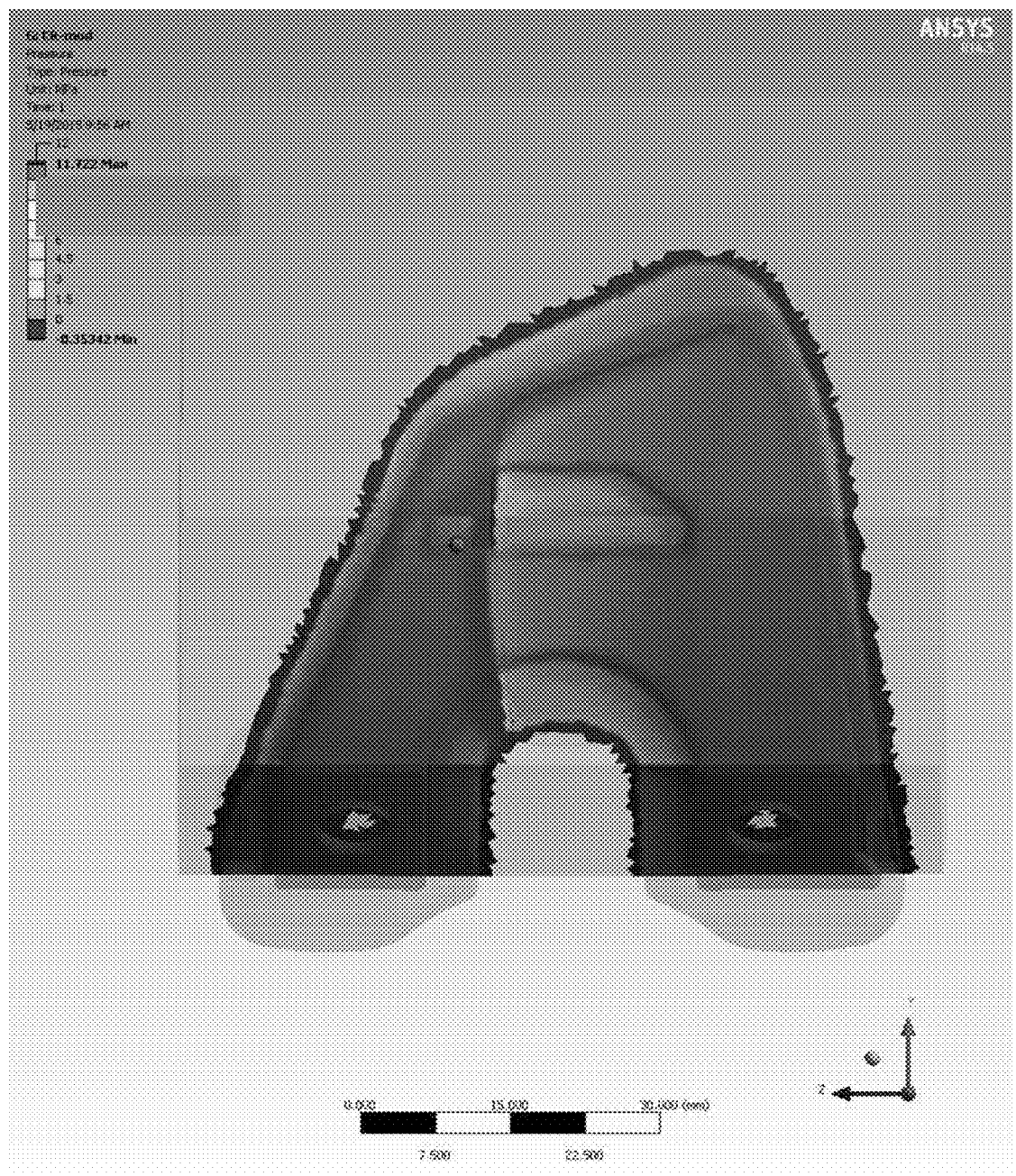
FIG. 9 is an image showing the normalized contact pressure distribution of the underlying bone upon testing a femoral component with a flexible anterior flange, such as the femoral component shown in FIG. 1.

FIGS. 7-9 show the superior results of a finite element analysis of a femoral component with a flexible anterior flange, such as femoral component 100, when compared with a standard femoral component. The testing conditions are shown in FIG. 7, in which a femoral component to be tested is depicted adjacent a patellar loading device. The tested femoral components were of cobalt chromium material and were loaded with a polymer patella. Bone cement was applied to fix the femoral component, and a stair climb activity was performed to achieve 60 degree knee flexion and a 38 degree patelofemoral angle. A compressive patella load of 3271 N was applied. The patient's body weight was 267 lbs., on average plus two standard deviations, with a body weight multiplier of 2.75.

FIG. 8 shows the normalized contact pressure distribution of the underlying bone for a standard femoral component. It is clearly shown that the contact pressure distribution of the bone for a standard femoral component is relatively even. FIG. 9 shows the normalized contact pressure distribution of the underlying bone for a femoral component with a flexible anterior flange, such as femoral component 100. The contact pressure distribution of the bone for a femoral component with a flexible anterior flange, such as femoral component 100, however, is much more varied, particularly adjacent a region that coincides with the location of slot 60. In particular, more of the contact pressure is distributed adjacent the area where slot 60 allows flexing of the patellar track, or intercondylar notch 30. This quantitative evidence displays the superior results that are achieved by a flexible patella-femoral articular surface of a monolithic femoral component 100, which reduces the potential for stress shielding and bone resorption on the underlying bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthesis comprising:
  a body including an articular surface and a bone-contacting surface opposite the articular surface, the articular and bone-contacting surfaces located within an edge of the body,
  wherein a slot extends through the articular and bone contacting surfaces, a first end of the slot passing through the edge and a second end of the slot located away from the edge,
  wherein the body is a femoral component, and the articular surface includes medial and lateral condylar articular surfaces and an intercondylar articular surface, the slot partially disconnecting the medial and lateral condylar articular surfaces to define a cantilever beam including the intercondylar articular surface,
  wherein a width of the slot is substantially constant along a majority of a length of the slot, and
  wherein a dimension of the slot at the second end is larger than the substantially constant width of the slot.

2. The prosthesis of claim 1, wherein the body is flexibly configured to transfer loads from the articular surface directly to resected femoral bone.

3. The prosthesis of claim 1, wherein the slot at least partially separates the medial condylar articular surface from the cantilever beam.

4. The prosthesis of claim 1, wherein a width of the slot is less than 10% of a width of the entire body measured along the same direction.

5. The prosthesis of claim 1, wherein the slot extends along a path that is generally L-shaped.

6. A knee prosthesis comprising:
  a monolithic femoral component including medial and lateral condylar elements for confronting and engaging a natural tibia or a bearing member of a tibial component, an intercondylar notch between the medial and lateral condylar elements for confronting and engaging a natural patella or a patellar component, and an anterior flange extending proximally from the medial and lateral condylar elements and the intercondylar notch,
  wherein the femoral component defines a bone-facing surface and a bearing surface, the bearing surface including medial and lateral condylar articular surfaces defined by the medial and lateral condylar elements, respectively, and an intercondylar articular surface defined by the intercondylar notch,
  wherein a slot extends through the femoral component from the bearing surface to the bone-facing surface, the slot starting at an edge of the femoral component and ending at a location within the anterior flange, and
  wherein the slot starts at a medial-distal intersection of the intercondylar notch and the medial condylar element and extends proximally along a medial edge of the intercondylar notch.

7. The knee prosthesis of claim 6, wherein the slot further extends laterally along a proximal region of the anterior flange.

8. The knee prosthesis of claim 6, wherein the slot partially disconnects the medial and lateral condylar articular surfaces to define the intercondylar notch as a cantilever beam.

9. The knee prosthesis of claim 8, wherein the slot at least partially separates the medial condylar element from the cantilever beam.

10. The knee prosthesis of claim 6, further comprising a tibial component including a bearing member.

11. The knee prosthesis of claim 6, further comprising a patellar component.

12. The knee prosthesis of claim 6, wherein a width of the slot is less than 10% of a width of the femoral component measured along the same direction.

13. The knee prosthesis of claim 6, wherein a width of the slot is substantially constant along a majority of a length of the slot.

14. The knee prosthesis of claim 13, wherein a dimension of the slot at the location within the anterior flange at which the slot ends is larger than the substantially constant width of the slot.

15. The knee prosthesis of claim 6, wherein the slot extends along a path from a location at the edge of the femoral component to the end location within the anterior flange that measures at least ten times a width of the slot.

16. The knee prosthesis of claim 6, wherein the slot extends along a path that is generally L-shaped.

17. A method of making the knee prosthesis of claim 6, comprising the steps of:
　cutting the slot in the monolithic femoral component,
　wherein the step of cutting includes cutting the slot to extend through the femoral component from the bearing surface to the bone-facing surface, and cutting the slot such that the slot starts at the edge of the femoral component and ends at the location within the anterior flange.

* * * * *